(12) United States Patent
McCoy et al.

(10) Patent No.: US 6,485,706 B1
(45) Date of Patent: Nov. 26, 2002

(54) FORMULATIONS COMPRISING DEHYDRATED PARTICLES OF PHARMA-CEUTICAL AGENTS AND PROCESS FOR PREPARING THE SAME

(75) Inventors: Randall McCoy, McConnellsburg, PA (US); Miles Augustus Libbey, III, Pennington, NJ (US); Jle Liu, Scotch Plains, NJ (US); Robert O. Williams, III, Austin, TX (US)

(73) Assignee: DelRx Pharmaceutical Corp., Jamesburg, NJ (US)

( * ) Notice: Subject to any disclaimer, the term of this patent is extended or adjusted under 35 U.S.C. 154(b) by 0 days.

(21) Appl. No.: 09/586,007

(22) Filed: Jun. 2, 2000

Related U.S. Application Data

(62) Division of application No. 09/502,871, filed on Feb. 11, 2000.
(60) Provisional application No. 60/137,562, filed on Jun. 4, 1999.

(51) Int. Cl.7 .............................. A61K 9/12; A61K 9/10; A61K 38/10; A61K 38/12
(52) U.S. Cl. ............................ 424/45; 424/54; 424/46; 424/49; 424/491; 514/2; 514/3
(58) Field of Search .............................. 424/54, 46, 45, 424/49, 491; 514/2, 3

(56) References Cited

U.S. PATENT DOCUMENTS

| | | | |
|---|---|---|---|
| 4,153,689 A | 5/1979 | Hirai et al. .................. 424/178 |
| 4,294,829 A | 10/1981 | Suzuki et al. ................ 424/177 |
| 4,476,116 A | 10/1984 | Anik .......................... 424/241 |
| 4,548,922 A | 10/1985 | Carey et al. .................... 514/4 |
| 4,648,393 A | 3/1987 | Landis et al. ........... 128/200.23 |
| 4,746,508 A | 5/1988 | Carey et al. ................... 424/88 |
| 4,835,142 A | 5/1989 | Suzuki et al. ................. 514/53 |
| 4,925,673 A | 5/1990 | Steiner et al. ............... 424/455 |
| 4,976,968 A | 12/1990 | Steiner |
| 4,994,439 A | 2/1991 | Longenecker et al. ......... 514/3 |
| 5,011,678 A | 4/1991 | Wang, et al. |
| 5,053,389 A | 10/1991 | Balschmidt et al. ............ 514/4 |
| 5,059,587 A | 10/1991 | Yamamoto et al. ........... 514/12 |
| 5,165,391 A | 11/1992 | Chiesi et al. .......... 128/200.23 |
| 5,190,029 A | 3/1993 | Byron et al. ........... 128/200.14 |
| 5,200,393 A | 4/1993 | Weiner .......................... 514/3 |
| 5,230,884 A | 7/1993 | Evans et al. .................. 424/45 |
| 5,284,657 A | 2/1994 | Lu et al. ..................... 424/435 |
| 5,320,094 A | 6/1994 | Laube et al. ........... 128/203.12 |
| 5,456,677 A | 10/1995 | Spector ..................... 604/290 |
| 5,487,898 A | 1/1996 | Lu et al. ..................... 424/435 |
| 5,518,998 A | 5/1996 | Backstrom et al. ............ 514/3 |
| 5,558,085 A | 9/1996 | Rubsamen et al. ..... 128/200.14 |
| 5,676,931 A | 10/1997 | Adjei et al. |
| 5,693,608 A | 12/1997 | Bechgaard et al. ............ 514/2 |
| 5,739,136 A | 4/1998 | Ellinwood, Jr. et al. .... 514/252 |
| 5,743,250 A | 4/1998 | Gonda et al. .......... 128/200.14 |
| 5,789,375 A | 8/1998 | Mukae et al. .................. 514/2 |
| 5,824,646 A | 10/1998 | Fujii et al. .................... 514/12 |
| 5,830,853 A | 11/1998 | Backstrom et al. ............ 514/4 |
| 5,874,064 A | * 2/1999 | Edwards et al. .............. 424/46 |
| 5,902,789 A | 5/1999 | Stoltz ............................ 514/4 |
| 5,906,811 A | * 5/1999 | Hersh .......................... 424/54 |
| 5,952,008 A | 9/1999 | Backstrom et al. ......... 424/499 |
| 5,981,591 A | 11/1999 | Deihl ......................... 514/568 |
| 5,989,539 A | 11/1999 | Leone-Bay et al. ........ 424/85.2 |

* cited by examiner

Primary Examiner—Jose' G. Dees
Assistant Examiner—M. Haghighatian
(74) Attorney, Agent, or Firm—Mathews, Collins, Shepherd & McKay

(57) ABSTRACT

A formulation for non-invasive delivery of pharmaceutical agents, particularly proteins and peptides, by absorption through a membrane at a targeted site is provided, along with a process of making the formulation. The formulation comprises a suspension of solid-phase dehydrated particles in a delivery medium. The particles comprise the dehydration product of the pharmaceutical agent and at least one of a surfactant and permeation enhancer, and the delivery medium preferably comprises a propellant for pressurized aerosol delivery of the formulation. The formulation can be conveniently delivered to the patient's targeted site where the pharmaceutical agent is absorbed through the mucosa to achieve a desired bioavailability.

19 Claims, 2 Drawing Sheets

```
pharmaceutical          Buffer,
agent                   pH adjustments
      1A                                      1
                             │
                             ▼
surfactant              pharmaceutical agent/       P.E.
                        buffer solution
      2A                                    2        2B
                             │
                             ▼
                        dehydration to solid-
                        phase particles
                                             3
                             │
                             ▼
solvent or cosolvent    dehydrated solid-phase
(optional excipients)   particles in slurry
      4B                                     4
                             │
                             ▼
metering valves         pressure-resistant containers;
                        valves crimped
      5A                                     5
                             │
                             ▼
propellant(s)           formulation in delivery
(opional                medium for aerosol spray
excipients)   6A        delivery              6
```

*Fig. 1*

FORMULATIONS COMPRISING DEHYDRATED PARTICLES OF PHARMA-CEUTICAL AGENTS AND PROCESS FOR PREPARING THE SAME

RELATED APPLICATIONS

This application is related to, and claims the benefit of priority under, U.S. provisional patent aplication Ser. No. 60/137,562, filed Jun. 4, 1999. The application also is a division of U.S. patent application Ser. No. 09/502,871, filed Feb. 11, 2000, which is incorporated herein by reference.

BACKGROUND OF THE INVENTION

1. Field of the Invention

The present invention relates to formulations for delivery of pharmaceutical agents such as therapeutic proteins and peptides by non-invasive routes to patients and to processes for preparing the formulations.

2. Description of the Prior Art

Effective, convenient, and comfortable delivery of pharmaceuticals to patients (both human and animal) is an area of major concern for a number of drugs. Various forms of pharmaceutical compositions and carrier agents are continually being developed to enhance the effectiveness and timing of drug delivery. Issues such as compositional stability, patient convenience, and difficulty in fabrication (e.g., cost) often need to be considered as formulations and delivery methods are developed, thus complicating the developmental process.

A conventional mode of delivery for many drugs is by oral ingestion of pills or tablets that disintegrate into primary particles and release the drug for absorption into the patient's bloodstream from the stomach and gastrointestinal (GI) tract. However, there are many proteins and peptides that, while effective 5 therapeutically, are not suitable for conventional modes of delivery such as oral delivery, as they are susceptible to enzymatic degradation, and the large size and hydrophobic nature of these therapeutic agents makes them ill-suited for absorption through the GI tract. Saliva and gastrointestinal enzymes tend to degrade or digest the pharmaceutical agents, rendering them ineffective. Examples of such agents include insulin, leuprolide, human growth hormones, and others.

Traditionally, proteins or peptides have been delivered by parenteral routes to overcome those difficulties and obtain a desirable bioavailability. However, parenteral delivery, e.g., by injection, causes great discomfort and significant 15 inconvenience to patients, and consequently results in poor patient compliance, especially when the therapy is intended for treating chronic diseases, such as diabetes. A noninvasive delivery route is thus in order so that proteins and peptides can be administered to patients to achieve a desired bioavailability without the pain and discomfort associated with parenteral delivery.

Efforts have been directed toward developing less invasive routes to administer proteins and peptides. For example, one approach involves encapsulating the protein in a microsphere so that the insulin is protected from degradation until it hits the targeted site (e.g., the intestines), at which point the microsphere decomposes to release the insulin. See, e.g., U.S. Pat. No. 4,925,673 to Steiner, "Delivery Systems for Pharmacological Agents Encapsulated with Protenoids" issued May 15, 1990; U.S. Pat. No. 4,976,968 to Steiner, "Anhydrous Delivery Systems for Pharmacological Agents," issued Dec. 11, 1990, and U.S. Pat. No. 5,503,852 to Steiner et al., "Method for Making Self-assembling Diketopiperazine Drug Delivery System," issued Apr. 2, 1996, all of which are incorporated herein by reference. Delivery systems using microparticles may be pH sensitive; that is, they rely upon changes in pH along the patient's digestive tract to cause degradation of the microsphere and release the encapsulated pharmaceutical agent. Similarly, compounds useful in developing a pharmaceutical composition for pill delivery of such agents are disclosed in U.S. Pat. Nos. 5,990,166 and 5,989,539 to Leone-Bay et al. These delivery mechanisms have drawbacks in that, among other things, the pharmaceutical agents are not immediately released into the bloodstream as the microsphere (or pill) must first travel to the patient's gastrointestinal tract, disintegrate into primary particles, and be digested.

Efforts have been made to develop formulations effective for more immediate delivery of proteins and peptides through the patient's pulmonary system or respiratory tract via inhalation. For example, U.S. Pat. Nos. 5,952,008, 5,830,853, 5,518,998, and 5,506,203, each incorporated herein, issued to Backstrom et al., disclose preparations in the form of a dry powder that include insulin pulverized to a small (<10 micron) size and an enhancer compound for inhalation delivery to the lower respiratory tract. Formulations for enhancing absorption through the nasal membranes are disclosed in various patents including U.S. Pat. No. 5,902,789 to Stoltz, U.S. Pat. No. 5,112,804 to Kowarski, U.S. Pat. No. 5,693,608 to Bechgaard, and U.S. Pat. No. 5,059,587 to Yamamoto et al. Many formulations designed to increase effectiveness in delivery to the pulmonary system include use of steroids or acids, such as carboxylic acids, furidic acid, amino acids, glycyrrhetinic acid, glycytrhizic acid, organic acids such as succinic acid, tartaric acid, and so forth, which may be disadvantageous to the patient's overall well-being.

A recent aerosol formulation for delivery of proteins and peptides is disclosed in US Pat. No. 5,230,884 to Evans et al., "Aerosol Formulations Including Proteins and Peptides Solubilized in Reverse Micelles and Process for Making the Aerosol Formulations" (incorporated herein). The Evans '884 patent discloses an aerosol formulation to deliver polypeptides and proteins to the pulmonary region. The '884 patent discloses that reverse micelle systems were formed. The micelles were emulsified in the hydrophobic propellant phase in the presence of surfactants, and the therapeutic agent was dissolved in the aqueous core of the micelles. However, the '884 patent acknowledges the extreme difficulty in preparing the reverse micelle system as disclosed in that patent, and additionally, the micelles were adapted for delivery via the pulmonary region.

There are adverse long-term health effects associated with inhalation delivery of pharmaceutical agents. Additionally, when the pharmaceutical agents are delivered by spraying in the mouth with breath-activated inhalation, much of the drug remains in the mouth and degrades, without being absorbed into the bloodstream. This reduces the bioavailability of the drug, increases the cost to the patient, causes local and systemic side effects such as ehrush, and requires administration of larger doses of drug to achieve the same effect.

As may be appreciated, those in the field of pharmaceuticals continue to search for new pharmaceutical compositions and methods of delivery that more effectively and immediately deliver pharmaceutical agents to a patient, while maximizing patient convenience and comfort, compositional stability, and minimizing the difficulties and costs of fabrication.

SUMMARY OF THE INVENTION

The present invention comprises a formulation for non-invasive delivery of pharmaceutical agents, particularly proteins and peptides, by absorption through a membrane at a targeted site. The formulation comprises a suspension of solid-phase dehydrated particles in a delivery medium, wherein the particles comprise the dehydration product of the pharmaceutical agent and at least one of a surfactant and permeation enhancer. The delivery medium preferably comprises a fluid such as a propellant for pressurized aerosol delivery of the formulation to the patient's targeted site where the pharmaceutical agent is absorbed through the mucosa. According to one aspect of the invention, the pharmaceutical agent comprises insulin; the surfactant is selected from Span, Tween, Brij, and Pluronic surfactants; and the permeation enhancer is selected from sodium lauryl sulfate, sodium laurate, and derivatives thereof. Each dose of pharmaceutical agent may be administered with a delivery system including a container, a metering pump or valve fitted to the container, and an actuator, such that a single dose may be administered by actuating the metering pump or valve fitted to the container.

The present invention also comprises a process for preparing a formulation suitable for mucosal absorption at a targeted site comprising preparing a solution of pharmaceutical agent with buffer, to which is added surfactant and/or permeation enhancer; dehydrating the solution to obtain solid-phase particles; and suspending the particles in a delivery medium.

BRIEF DESCRIPTION OF THE FIGURES

For a better understanding of the invention, exemplary embodiments are described below, considered together with the accompanying figures, in which:

FIG. 1 is a block diagram of steps of one exemplary embodiment of the inventive process.

DETAILED DESCRIPTION OF THE INVENTION

Figure 2:
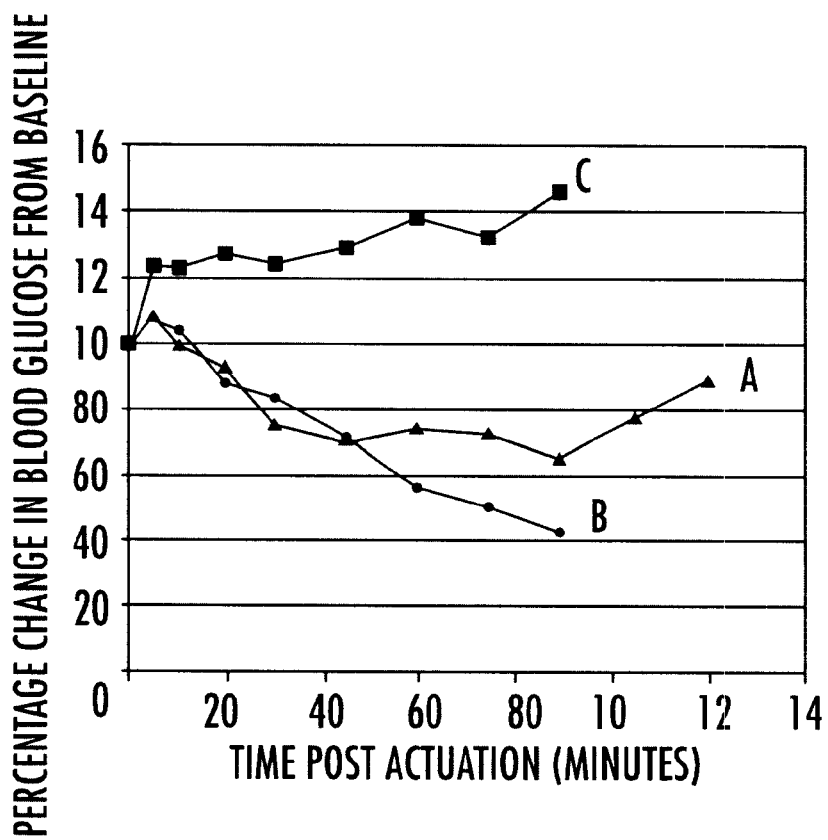
FIG. 2 is a graph plotting the percentage change in blood glucose as a function of time upon delivery of the inventive formulation including insulin to rats.

This invention provides a formulation useful for delivering pharmaceutical agents, such as therapeutic proteins and peptides, to a targeted area for absorption through an epithelial membrane. By epithelial membrane is meant a surface membrane or cell structure at the patient's targeted site. In this formulation, dehydrated solid-phase particles comprised of an active pharmaceutical agent and at least one of a surfactant and permeation enhancer are suspended in a pharmaceutically-acceptable delivery medium, optionally in the presence of ethanol. The delivery medium is a fluid (e.g., liquid, gas, or atomized spray) to aid in transporting the solid-phase dehydrated particles to the targeted site. The aerosol spray formulation is designed so that it is suitable for delivery of the drug to the buccal cavity or the sublingual area for absorption through the mucosa. Although targeted areas other than the buccal cavity are contemplated, the formulation is configured such that when sprayed intraorally, delivery to the pulmonary region (e.g. through inhalation) is avoided or minimized, thereby enhancing bioavailability and reducing risks associated with pulmonary delivery. The delivered formulation is transported through the cell membrane at the targeted area and reaches the systemic blood circulation.

With this invention, the formulation may be delivered via an atomized spray or liquid, thereby avoiding the pains and discomfort encountered with parenteral injections when administering therapeutic proteins and peptides. Advantageously the delivery medium comprises a pharmaceutically-acceptable propellant, and the formulation is contained in a pressure-resistant container suitable for aerosol delivery of the drug. A metering pump or valve and an actuator may be fitted to the container, such that a single dose may be administered by actuating the metering pump or valve. The invention is applicable to various non-invasive routes of drug administration, including buccal, sublingual, and nasal delivery. By co-administration of the therapeutic agent and permeation enhancers at the targeted region, the permeability of the cell membrane is increased, thereby allowing for absorption through the epithelial membrane at the target area and increasing the bioavailability of the therapeutic agent. The percentage of surfactant and/or permeation enhancers used in the formulation may be adjusted to control the timing of drug absorption in the blood stream. Additionally, the inventive formulations have demonstrated superior stability and shelf-life as compared with previous formulations of therapeutic proteins and peptides, particularly as applied to insulin which traditionally has required refrigeration to maintain its stability over a period of time.

The invention also comprises an advantageous method of preparing such a formulation. The process involves mixing the pharmaceutical agent in a pharmaceutically-acceptable buffer such as acetate buffer, lactate buffer, Tris buffer, phosphate buffer, or the like, to form a solution with a target pH, e.g., in the range of 3 to 8. The solution is mixed with at least one of a pharmaceutically acceptable surfactant or permeation enhancer, and then the solution is dehydrated such as by lyophilization to form dehydrated, solid-phase particles. The solid-phase particles are suspended in a delivery medium comprising a non-solubilized fluid. This process yields a suspension that can be re-configured readily into a homogenous dispersion upon gentle agitation. The formulation is capable of reproducibly delivering an accurate amount of pharmaceutical agent at each actuation.

The pharmaceutical agents suitable for the formulation include insulin, interferon, oxytocin, leuprolide acetate, luteinizing-hormone releasing hormone (LHRH) analogs, DNase, human growth hormone, and alpha-antitrypsin. Insulin (human, bovine, or porcine) is discussed herein as one exemplary pharmaceutical agent. Advantageously, the pharmaceutical agent will be present in the formulation in an amount of from 0.01 to 25% by weight. For example, an exemplary embodiment using insulin comprises about 0.5 to 1% by weight insulin.

The surfactant and permeation enhancer may comprise a single compound that functions to increase the miscibility of the formulation ingredients by reducing interfacial tension between the solid dehydrated particles and the propellant and to prepare the mucosa for absorption of the pharmaceutical agent. However, typically the surfactant and permeation enhancer will comprise separate compounds or compositions. Suitable surfactants that can used in the formulation include sorbitan monooleate (Span 80), sorbitan monolaurate (Span 20), lecithin, oleic acid, polyoxyethylene sorbitan monolaurate (Tween 20), polyoxyethylene sorbitan monooleate (Tween 80), polyoxyethylene 2 oleyl ether (Brij 92), polyoxyethylene 10 oleyl ether (Brij 97), polyoxyethylene 20 oleyl ether (Brij 98), Pluronic such as Pluronic F77, and dioctyl sodium sulfosuccinate (Aerosol OT). The appropriate level of surfactants in the formulation ranges from 0.01% w/w to 20% w/w.

Permeation enhancers increase membrane permeability and facilitate drug transport through the biological membrane, thereby improving the bioavailability of the delivered therapeutic agent. The permeation enhancers may comprise "oral absorption enhancers" as described in U.S. patent application Ser. No. 09/502,871, which function to increase permeation across a surface membrane of the intra-oral cavity. Suitable membrane-permeation enhancers include surfactants such as sodium lauryl sulfate, sodium laurate, palmitoyl carnitine, Laureth-9, phosphatidylcholine, cyclodextrin and derivatives thereof, bile salts such as sodium deoxycholate, sodium taurocholate, sodium glycochlate, and sodium fusidate, chelating agents including EDTA, citric acid and salicylates, and fatty acids (e.g., oleic acid, lauric acid, acylcarnitines, mono- and diglycerides). Other membrane-permeation enhancers may include benzalkonium chloride, benzethonium chloride, CHAPS (3-(3-cholamidopropyl)-dimethylammonio-1-propane-sulfonate), BigCHAPS (N,N-bis-(3-D-gluconamido-propyl) cholamide), chlorobutanol, octoxynol-9, benzyl alcohol, phenol, cresol, and alkyl alcohols. The preferred level of permeation enhancers in the formulation is 0.1% w/w to 80% w/w.

The solid-phase dehydrated particles of pharmaceutical agent, surfactant and/or permeation enhancer are sized for the targeted area. Typically, the particles will be sized in the range of about 10–500 microns in diameter, more preferably having a diameter d in the range of 10<d<200 microns. It is not necessary or desirable in practicing the invention that the particles be micronized, such as by pulverization, to sizes of less than 10 microns, as the formulation of this invention is configured for intra-oral delivery and absorption through buccal epithelial membrane while avoiding delivery through the pulmonary region. Delivery to the respiratory tract would require particles sized smaller than 10 microns, more specifically in the 2 to 5 micron range, and thus, with this invention, advantageously a substantial percentage of the particles are sized at 10 microns and above in diameter. The cooling rate at which the particles are dehydrated and method of dehydration may be controlled to adjust the particle size. Use of such dehydrated solid-phase particles enhances the is stability of the pharmaceutical agent in the formulation.

The solid-phase dehydrated particles are suspended in a delivery medium which preferably comprises a non-aqueous propellant system. The propellant system for a propellant-driven aerosol formulation consists of one or a combination of pharmaceutically acceptable propellants, including hydrofluorocarbons (HFA 134a, HFA 227), chlorofluorocarbons (CFC 11, CFC 12, CFC 114), hydrocarbons (propane, butane, isobutane, etc.), and dimethyl ether. HFA 134a and HFA 227 are preferred propellants due to the restriction in production and use of CFC propellants. Typically, the propellants will be present in the formulation in an amount of 20–99% by weight, more preferably in the range of 50–80% by weight.

Ethanol can be incorporated into the formulation as a dispersing aid and a cosolvent for the surfactants, with its level ranging from 0% w/w to 20% w/w. A typical level of ethanol in the formulation is 8–12% w/w. Other solvents or co-solvents may used such as glycerol, propylene glycol, polyethylene glycol, sorbitol, vitamin E and derivatives of vitamin E, polyvinylpyrrolidone, water, and other orally-acceptable solvents known in the field.

A non-aqueous based delivery system provides many advantages. For example, it enhances the stability of the pharmaceutical agent in the formulation, the miscibility of the solid-phase particles in the delivery medium, and the aerosol delivery of the particles to the targeted site. The density of propellants typically is above 1.2, or at least 10 percent greater than the density of water. With use of the non-aqueous system, the density of the system (or carrier fluid(s) in which the pharmaceutical agent is suspended) can be controlled to match the density of the propellant. Thus, there is an increase in suspension time (e.g., the amount of time that the particles will remain suspended in the system). Additionally, the pharmaceutical agents may polymerize in the presence of water, such that a non-aqueous system enhances the stability of the drug.

However, if an aqueous-based aerosol delivery system is prepared, the formulation advantageously should be preserved against microbial growth since this may affect the chemical stability of the ingredients, safety, and acceptability of the product, and the physical integrity of the system. Parabens and benzalkonium chloride are exemplary, effective anti-microbial agents. The amount of such agents will depend upon the volume of water and formulation ingredients and can be determined by one skilled in the field with use of micro-organism growth tests. Typically, the anti-microbial agent will be present in the formulation on the order of up to 5% by weight. Known methods for ensuring the preservation of aqueous parenteral products as approved by the FDA are applicable to this invention.

Optionally, the formulation may include other excipients such as viscosity/mucoadhesive enhancing agents including cellulose ether polymers and chitosan; flavoring agents; preservative systems including benzoic acid, benzyl alcohol, thimerosal, phenylethyl alcohol, benzethonium chloride, methyl paraben, ethyl paraben, butyl paraben or propyl paraben; anti-oxidants; kelating agents; agents to adjust osmolarity; agents to adjust pH; and non cross-linked polymers.

The formulation can be transferred to or mixed in a container for pump or propellant delivery. For example, to prepare a propellant-driven aerosol, the obtained dehydrated solid phase particles can be dispersed in ethanol, if desired, to form a homogenous dispersion which then may be transferred to a pressure-resistant container. A metering valve that is suitable for accurate and reproducible delivery of aerosol doses may be fitted and crimped to the container, and one or a combination of liquefied propellants can be filled into the container to form a suspension system containing the dehydrated solid-phase particles composed of pharmaceutical agent and functional excipients. The obtained formulation can be used as a pressurized metered-dose applicator (pMDA™) suitable for aerosol delivery by propellant or metered-valve non-propellant systems. Other types of delivery mechanisms for administering the formulation to a targeted size in metered doses may be used. For example, the formulation can be prepared in a gel capsule or small tube, optionally having a nozzle thereon, for delivering predetermined units of formulation. For the topical mode of administration, the formulation can be packaged in the form of a metered-dose applicator (MDA™) and sprayed directly to the targeted sites of the body, which include, but are not limited to the buccal mucosa, sublingual area and skin. Metal, glass, plastic, or other types of containers can be used.

It will be appreciated that the invention can be used to treat a large variety of diseases, including diabetes, male hypogonadism, impotence, pain management, and osteoporosis, as well as diseases and disorders requiring the administration of small and large molecule proteins and peptides.

According to one aspect of the invention, an exemplary process of preparing an inventive formulation and system for aerosol delivery is set forth in the block diagram of FIG.

1. In Blocks 1A-1, a quantity of pharmaceutical agent (block 1A) is mixed with a pharmaceutically acceptable buffer (block 1), such as Tris buffer, lactate buffer, phosphate buffer, or the like. The amount of the pharmaceutical agent may be determined by one skilled in the field depending upon the final dosage unit sought to be achieved, the formulation ingredients, the anticipated delivery mechanism, and the targeted site. For example, in preparing a formulation for aerosol delivery of insulin to the buccal cavity, approximately 2–30 mg/ml of insulin may be added to the buffer solution to achieve a 0.5%–1% insulin formulation. The pH is adjusted to form a solution with a target pH. The target pH may be in the range of 3 to 8.

In Blocks 2, 2A, and 2B, surfactant (Block 2A) and permeation enhancer (Block 2B) are mixed with the pharmaceutical agent/buffer solution and stirred to obtain a uniform solution. The surfactants and the membrane-permeation enhancer are preferably soluble in water, such that a homogeneous solution is formed in Block 2. This mixing may be achieved by the pharmaceutical agent/buffer solution being volumetrically added to vials containing surfactant and permeation enhancer. Other ingredients such as excipients that are soluble in the buffer solution may be added at this point.

In Block 3, the solution containing the pharmaceutical agent, surfactant and permeation enhancer is dehydrated to form solid-phase particles. Optionally, the solution may be filtered before or after the dehydration (such as by aseptic filtering) to remove impurities. The dehydration may be achieved with freeze-drying, e.g., advantageously at temperatures of below −10° C. to −40° C., more preferably at temperatures of below −20° C. The rate of freeze-drying and temperature used will impact upon the size of the crystals or solid-phase particles obtained, which in turn may impact upon the rate at which the pharmaceutical agent is released into the patient's bloodstream. Other methods of dehydration known in the field may be used such as critical point drying with $CO_2$ under pressure, solvent substitution, vacuum, or blow drying (e.g., in a nitrogen atmosphere). Lyophilization using temperatures in the range of −10° C. to −40° C. is preferred.

In blocks 4-4A, solvents or co-solvents, e.g., anhydrous ethanol, are added to the solid-phase particles to obtain a slurry composed of suspended particles with a substantial percentage of the particles in the 10 to 50 micron size range, optionally also with further excipients. To prepare an aerosol formulation, the slurry is transferred to a pressure-resistant container (block 5), a metering valve is fitted to the container (block 5A), and the valve is crimped. One or more propellants, such as HFA 134a (block 6A) and optionally excipients, may be filled into the container to provide a formulation comprising a suspension system of solid-dehydrated particles containing the pharmaceutical agent, surfactant, and permeation enhancer. The aerosol formulation is shaken, stored inverted, and can be delivered as an aerosolized dose with a metering valve system. The steps of blocks 5A-5 and 6A-6 may be adjusted depending upon the delivery system sought to be used.

The invention will be better understood from the following Examples. However, those of ordinary skill in the art will readily understand that these Examples are merely illustrative of the invention that is defined in the claims that follow thereafter. The reference to insulin in these Examples means human, bovine, or porcine insulin, unless otherwise noted.

EXAMPLE 1

Insulin was weighed in a clean glass container and dissolved in acid buffer and titrated to a pH of 7 with Tris buffer. Brij 98 and sodium lauryl sulfate were added to the insulin solution to form a homogenous solution. The mixture was lyophilized, and the dried solid particles were suspended in a non-aqueous suspension medium of ethanol and then charged with hydrofluoroalkane (HFA) 134a. The formulation was contained in a pressure-resistant container which was fitted with a metering valve. The composition of the formulation is presented as follows:

TABLE 1

| Composition of Formulation A | |
|---|---|
| Concentration of Each Pharmaceutical Ingredient (Percentage is expressed on w/w basis) | |
| Insulin | 1.0% |
| Brij 98 | 0.9% |
| Sodium Lauryl Sulfate | 1% |
| Anhydrous Ethanol | 20% |
| HFA 134a | q.s to 100% |

The formulation was presented as a readily redispersible suspension in which insulin solid was suspended in HFA 134a. The aerosol formulation delivered 36.04 IU of insulin upon a single actuation; this formulation is referred to below in Examples 4 and 5 as "Formulation A."

EXAMPLE 2

The composition of the formulation is presented as follows:

TABLE 2

| Composition of Formulation B | |
|---|---|
| Concentration of Each Pharmaceutical Ingredient (Percentage is expressed on w/w basis) | |
| Insulin | 1.0% |
| Brij 98 | 0.9% |
| Sodium Lauryl Sulfate | 5% |
| Anhydrous Ethanol | 20% |
| HFA 134a | q.s to 100% |

The aerosol delivered approximately 33.66 IU of insulin at each actuation. The formulation of this example is referred to below in Examples 4 and 5 as "Formulation B."

EXAMPLE 3

The composition of the formulation is presented as follows:

TABLE 3

| Composition of Formulation C | |
|---|---|
| Concentration of Each Pharmaceutical Ingredient (Percentage is expressed on w/w basis) | |
| Insulin | 1.0% |
| Pluronic | 0.9% |
| Sodium Lauryl Sulfate | 1% |
| Anhydrous Ethanol | 20% |
| HFA 134a | q.s to 100% |

EXAMPLE 4

The inventive formulation is capable of delivering an aerosol dose consistently upon being stored under ambient temperature over an extended period of time. Consistent physical and chemical attributes were maintained during the storage period at ambient conditions. Dose-Delivery-Through-the Valve (DDV) was monitored over a storage period of 3 months at ambient conditions for Formulations A, B, and C of Examples 1, 2 and 3, above, respectively, with two units of Formulations B and C. The results were as follows:

TABLE 4

DDV of the Propellant-Driven Human Insulin Aerosol Formulations

| Storage Period | DDV (IU per Actuation) | | | |
|---|---|---|---|---|
| (months) | Initial | 1 | 2 | 3 |
| Formulation A | 36.04 | 35.9 | 38.81 | 35.11 |
| Formulation B-Unit 1 | 32.34 | 33.66 | 35.38 | 34.06 |
| Formulation B-Unit 2 | 34.98 | 34.58 | 38.81 | 26.66 |
| Formulation C-Unit 1 | 32.6 | 35.24 | 35.64 | 31.66 |
| Formulation C-Unit 2 | 35.24 | 32.73 | 36.96 | 34.06 |

EXAMPLE 5

The major degradation product of human insulin is A-21 desamido-insulin, which was also determined for each aerosol dose collected in Example 4. The results were as follows.

TABLE 5

Stability of the Propellant-Driven Human Insulin Aerosol Formulations

| Storage Period at Ambient Conditions | Percentage of A-21 Desamido-Insulin In Each Aerosol Dose | | | |
|---|---|---|---|---|
| (months) | Initial | 1 | 2 | 3 |
| Formulation A | 0 | 0 | 0 | 0 |
| Formulation B-Unit 1 | 0 | 0 | 0 | 0 |
| Formulation B-Unit 2 | 0 | 0 | 0 | 0 |
| Formulation C-Unit 1 | 0 | 0 | 0 | 0 |
| Formulation C-Unit 2 | 0 | 0 | 0 | 0 |

Accordingly, various embodiments of the invention exhibited advantageous stability and dosing reproducibility over an extend storage period at ambient conditions. Most parenteral formulations for proteins and peptides require refrigerated storage conditions to circumvent chemical degradation of the active ingredient. In contrast, exemplary aerosol formulations according to this invention showed superior chemical stability after storage at ambient conditions for up to three months, suggesting that refrigerated storage conditions may not be necessary. This constitutes yet another advantage of this invention over previous compositions.

Although not intended to be bound by a particular theory, the inventors propose that the extraordinary stability of insulin in the foregoing formulations was attributed to the fact that the insulin exists in its solid phase while suspended in propellant media.

EXAMPLE 6

Human insulin aerosol formulations according to Examples 1–3 were administered to the buccal cavity of rats after fasting for overnight. Five actuations were delivered into the buccal cavity of each rat for each dose. Additionally, control groups of rats received buccal delivery of bovine insulin spray without pre-treatment of the buccal cavity and bovine insulin spray with pre-treatment. The pre-treatment consisted of a sodium lauryl sulfate swab to the cheek area. Aliquots of blood were collected periodically in the next two ours following dosing. Hypoglycemic effect was measured as the percent change in blood glucose concentration compared with the baseline. The results are presented in FIG. 2, where plot A reflects the percent change in blood glucose level for rats receiving the formulations according to this invention; plot B reflects the percent change in blood glucose level for rats receiving the bovine insulin spray with pre-treatment; and plot C reflects the percent change in blood glucose level for rats receiving the bovine insulin spray without pre-treatment. The treated rats and those receiving the inventive formulations reacted to the exogenous insulin as manifested by a profound decrease in blood glucose level within the first two hours immediately following dosing.

While the invention has been described in terms of its preferred embodiments, those skilled in the art will recognize that the invention can be practiced with modifications and variations within the spirit of the appended claims.

We claim:

1. A formulation for systemic delivery of insulin to a patient through the buccal mucosa, the formulation comprising:

a suspension of dehydrated solid particles in a delivery medium wherein the solid particles comprise a dehydration product of the insulin and an orally effective nonsteroidal membrane-permeation enhancer, the delivery medium comprising a fluid, the dehydrated solid particles being suspended in the delivery medium, and adapted for spray delivery of the dehydrated solid particles to the buccal mucosa.

2. The formulation of claim 1, said dehydrated solid particles further comprising a surfactant.

3. The formulation of claim 1 wherein a substantial percentage of the solid particles are greater than at least about 10 microns in diameter.

4. The formulation of claim 1, said delivery medium comprising a nonaqueous propellant for aerosol delivery of the dehydrated solid particles to the buccal mucosa.

5. The formulation of claim 2, said dehydrated solid particles comprising a dehydration product of a substantially homogeneous mixture of insulin, at least one buffer, at least one surfactant, and the membrane-permeation enhancer.

6. The formulation of claim 2 in which the surfactant is selected from a group consisting of sorbitan monooleate, sorbitan monolaurate, polyoxyethylene sorbitan monolaurate, polyoxyethylene sorbitan monooleate, polyoxyetilylene ethers, dioctyl sodium sulfosuccinate, and polyoxyethylene block copolymers.

7. The formulation of claim 1 adapted for aerosol delivery to the buccal mucosa wherein the insulin is substantially absorbed without reaching the pulmonary region.

8. The formulation of claim 1, the delivery medium comprising a non-aqueous pharmaceutically acceptable propellant and a co-solvent selected from the group consisting of ethanol, glycerol, propylene glycol, sorbitol, vitamin E, and polyvinylpyrrolidone.

9. The formulation of claim 2 comprising about 0.01 to 20% by weight surfactant; about 0.1 to 80% by weight membrane-permeation enhancer; and the delivery medium comprises about 50 to 99% by weight propellant and about 5 to 20% by weight ethanol.

10. The formulation of claim 2 in which the dehydrated solid particles comprise a freeze-dried dehydration product of a mixture consisting essentially of the insulin in buffer, a surfactant, and the non-steroidal membrane-permeation enhancer.

11. The formulation of claim 1 comprising a delivery medium further comprising a non-aqueous pharmaceutically-acceptable propellant, an alcoholic cosolvent and the dehydrated insulin particles further comprising a non-steroidal permeation enhancer and a pharmaceutically acceptable buffer.

12. A process for preparing a formulation for delivering a insulin to the buccal mucosa of a patient, the process comprising (a) obtaining a quantity of insulin;

(b) dissolving the insulin in a solution optionally containing a pharmaceutically acceptable buffet;

(c) mixing the solution with a non-steroidal membrane-permeation enhancer and optionally with a pharmaceutically acceptable surfactant;

(d) drying the solution of step (c) to form solid dehydrated particles; and (e) placing the solid dehydrated particles in a fluid to form a suspension for delivery of the solid particles to the patient's buccal mucosa for systemic absorption.

13. The process of claim 12, wherein the fluid comprises a pharmaceutically acceptable propellant and optionally ethanol.

14. A The process of claim 12, in which the solid particles are not pulverized and a substantial percentage of the particles are sized at greater than 10 microns.

15. The process of claim 12, wherein the step of drying comprises freeze-drying at temperatures in the range of −10° C. to −40° C.

16. The formulation of claim 5 in which the non-steroidal membrane-permeation enhancer is selected from a group consisting of sodium lauryl sulfate, sodium laurate, palmitoyl carnitin, Laureth-9, phosphatidylcholine, cyclodextrin, oleic acid, lauric acid, acylcarnitines, benz-alkonium chloride, benzethonium chloride, 3-3-cholamidopropyl)-dimethylammonio-1-propane-sulfonate, N,N-bis-(3-D-gluconamido-propyl)-cholamid), chlorobutanol, octoxynol-9, benzyl alcohol.

17. A method for systemic buccal administration of insulin to a patient in need of such treatment comprising:

administering solid particles in a pharmaceutically acceptable aerosol to the buccal mucosa, wherein the particles are at least about 10 $\mu$m about 500 $\mu$m in diameter and comprise a dehydration product of insulin and a non-steroidal buccal permeation enhancer and optionally further comprise a surfactant and pharmaceutically acceptable buffer.

18. The formulation of claim 1 wherein a substantial percentage of the solid-phase particles are sized greater than about 10 $\mu$m and less than about 500 $\mu$m in diameter.

19. The formulation of claim 1 wherein a substantial percentage of the solid-phase particles are sized greater than about 10 $\mu$m and less than about 200 $\mu$m in diameter.

* * * * *